United States Patent [19]

Sunahara et al.

[11] Patent Number: 5,108,905
[45] Date of Patent: Apr. 28, 1992

[54] METHOD OF ASSAYING MAGNESIUM IN HUMAN BODY FLUID

[75] Inventors: Yoshiko Sunahara; Shigeru Takata, both of Osaka; Isamu Takagahara, Chiba, all of Japan

[73] Assignee: Oriental Yeast Co., Ltd., Tokyo, Japan

[21] Appl. No.: 690,420

[22] Filed: Apr. 24, 1991

Related U.S. Application Data

[63] Continuation-in-part of Ser. No. 423,816, Oct. 18, 1989, abandoned.

[30] Foreign Application Priority Data

Nov. 29, 1988 [JP] Japan .................................. 63-299551

[51] Int. Cl.$^5$ .......................................... G01N 33/50
[52] U.S. Cl. ...................................... 435/26; 435/810; 436/79
[58] Field of Search ................ 435/4, 26, 810; 436/79

[56] References Cited

U.S. PATENT DOCUMENTS 4,657,854  4/1987  Wegfahrt .............................. 435/14
4,742,001  5/1988  Marui et al. .......................... 435/26

Primary Examiner—David L. Lacey
Assistant Examiner—David Redding
Attorney, Agent, or Firm—Browdy and Neimark

[57] ABSTRACT

Disclosed is a method of assaying the content of Mg ions in a human body fluid such as serum, urine or saliva by the use of a reactant solution containing isocitrate dehydrogenase, NADP+, isocitrate and an excess amount of a chelating agent. Almost all Mg ions as existing in a human body fluid sample to be examined are bonded with the chelating agent, and the remaining Mg ions react with NADP+ to form NADPH. Increase of the thus formed NADPH is measured to obtain a standard curve of a straight line, and the content of Mg ions in the same is determined on the basis of the standard curve. If such an excess amount of Mg-chelating agent is not added to the reactant solution, the intended standard could not be in the form of a straight line but is in the form of a tangent curve. Using the tangent curve, the content of Mg ions in the human body fluid sample cannot be assayed accurately.

1 Claim, 2 Drawing Sheets

STANDARD CURVE IN THE PRESENCE OF CHELATING AGENT

METHOD OF ASSAYING MAGNESIUM IN HUMAN BODY FLUID

This is a continuation-in-part of co-pending application Ser. No. 423,816, filed on Oct. 18, 1989, now abandoned.

FIELD OF THE INVENTION

This invention relates to a method of assaying magnesium in a human body fluid.

Magnesium occurs widely in the cells of animals and plants and is essential to their growth and life.

The quantity of magnesium in living bodies varies in an antagonistic relation to calcium, and its variation is observed in patients suffering from insufficiency of the central nervous system, heart, or kidney, acute pancreatitis, etc. Therefore, the assay of magnesium is becoming one of the important items of clinical examination.

The method of this invention enables a quick and accurate assay of magnesium in a human body fluid, and thereby contributes greatly to clinical examination.

PRIOR ART AND PROBLEMS

A colorimetric method which employs xylidyl blue to form a chelate is known for assaying magnesium. Atomic absorption spectrometry is another known method. Both of these methods, however, have drawbacks. The substance employed by the former method does not have a sufficiently high specificity to magnesium. The latter requires a special apparatus.

Still another method has been proposed, where a reactant solution containing isocitrate dehydrogenase, NADP+ and isocitrate is employed and the solution is reacted with Mg ions as a reaction trigger in accordance with the following reaction formula (I) whereupon the amount of NADPH to be formed by the reaction is measured as the absorbance thereof at 340 nm (U.S. Pat. No. 4,657,854).

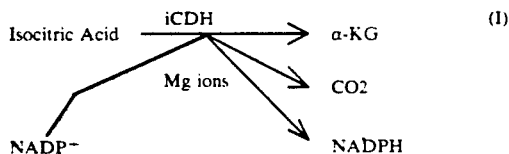

(I)

However, after assay of Mg ions in a human serum by the proposed method, an accurate result could not be obtained. As the reason, it has been found that even a small amount of Mg ions strongly reacts with the reactant isocitrate dehydrogenase to rapidly terminate the reaction of formula (I), as shown in FIG. 1.

MEANS TO SOLVE THE PROBLEMS

We, the inventors of this invention, have studied in detail the relations which may exist between magnesium and the activity of various kinds of enzymes, in order to find out a method which can determine the quantity of magnesium in human body fluids quickly and accurately. As a result, we have found that the following facts: Precisely, isocitrate dehydrogenase rapidly reacts with even a small amount of Mg ions. If an excess amount of a Mg-chelating agent is added to the reaction system of containing a human body fluid to be assayed, almost all Mg ions as existing therein are to be converted into its chelates. Thereafter the amount of the remaining Mg ions in the reaction system may be well assayed thereby to determine the amount of Mg ions in the human body fluid sample. On the basis of the finding, we have completed this invention.

Specifically, in accordance with the assaying method of this invention, an excess amount of a Mg-chelating agent is added to form a reactant solution, and a determined amount of a human body fluid (e.g., human serum) to be assayed is added to the reactant solution. Accordingly, the chelating agent first reacts with almost all the Mg ions in the human body fluid sample, and thereafter the remaining Mg ions are reacted with iCDH whereupon the absorbance of the resulting product at 340 nm may be determined to obtain an accurate content of Mg ions in the human body fluid sample.

Figure 2:
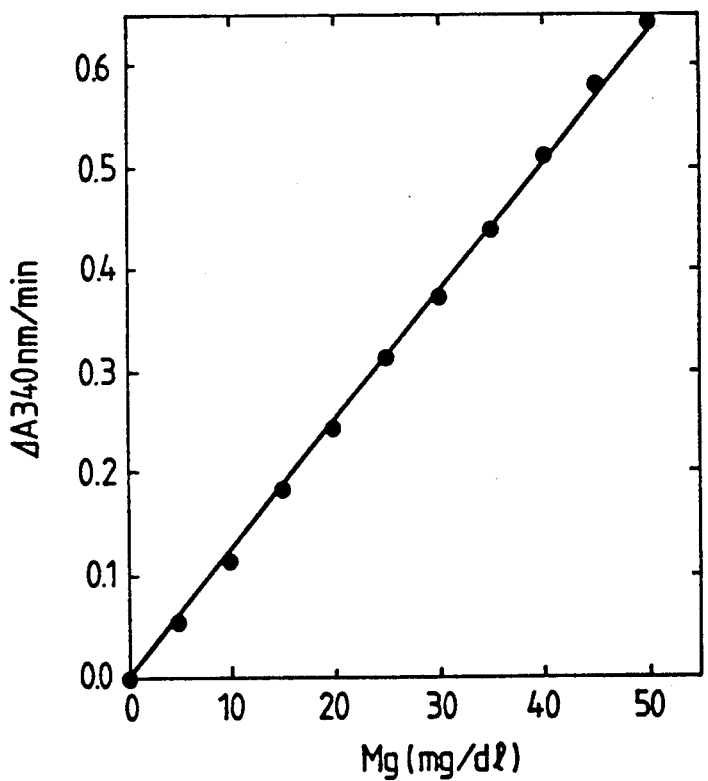
FIG. 2 shows the calibration curve of magnesium assay in the presence of an excess amount of a Mg-chelating agent, as obtained in Example 1.

In assaying the Mg ion content in a sample by this invention, it is necessary that a reactant solution containing an excess amount of a Mg-chelating agent is previously prepared and is added to a Mg ions-containing solution whereupon the absorbance of the reaction solution at 340 nm is measured in a determined period of time or by rate assay, in accordance with the method of Example 1, to thereby form a standard curve of FIG. 2. The standard curve of FIG. 2 is in the form of a straight line because of addition of such an excess amount of a Mg-chelating agent. For actually determining the Mg ion content in a human body fluid on the basis of the thus prepared standard curve of FIG. 2, the value to be obtained from the absorbance at 340 nm may be applied to and compared with the corresponding value of the standard curve of FIG. 2 to thereby accurately determine the Mg ion content in the human body fluid sample.

Figure 1:
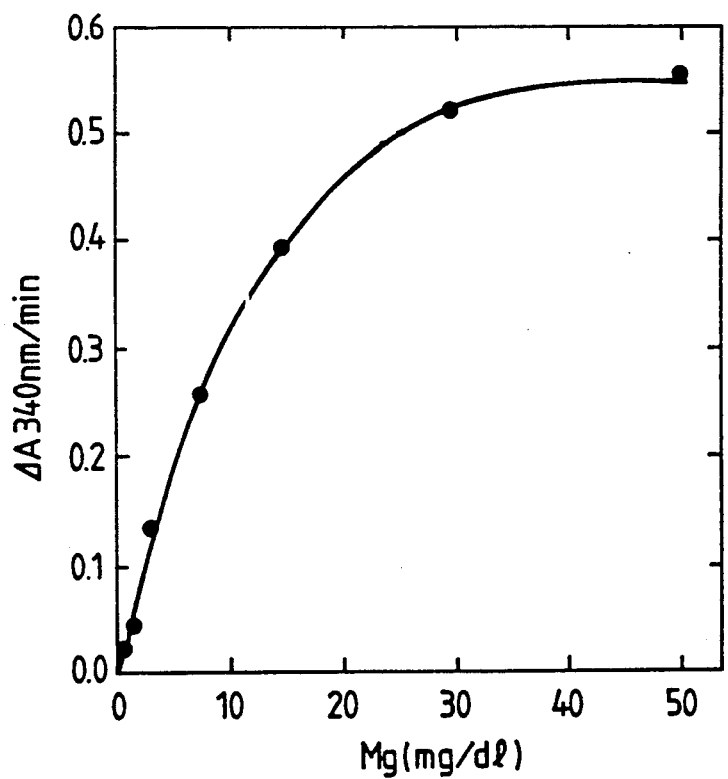
FIG. 1 shows the calibration curve of magnesium assay in the absence of a Mg-chelating agent.

As opposed to the method of the present invention, where assaying of Mg ions is effected in the same manner as in Example 1 except that no Mg-chelating agent is added to the reactant solution, as shown in Comparative Example (mentioned hereinafter), the tangent line of FIG. 1 is obtained. If the tangent line of FIG. 1 is used as the standard curve in assaying the Mg ion content in a human serum, an accurate value of the intended Mg ion content could not be obtained since the measured datum could not well correspond to that on the tangent line.

Examples of Mg-chelating agents usable in the method of this invention include the following substances and salts thereof:

EDTA; trans-1,2-cyclohexanediamine-N,N,N',N'-tetraacetic acid; N,N-di(hydroxyethyl)glycine; 1,3-diaminopropan-2-ol-N,N,N',N'-tetraacetic acid; diethylenetriamine-N,N,N',N'',N'''-pentaacetic acid; ethylenediamine-N,N'-diacetic acid; ethylenediamine-N,N'-dipropionic acid; N-hydroxyethylethylenediamine-N,N',N'-triacetic acid; ethylenediamine-N,N,N',N'-tetrakis(methylene-phosphonic acid); glycoletherdiamine-N,N,N',N'-tetraacetic acid; hexamethylenediamine-N,N,N',N'-tetraacetic acid; hydroxyethyliminodiacetic acid; iminodiacetic acid; 1,2-diaminopropane-N,N,N',N'-tetraacetic acid; nitrilotriacetic acid; nitrilotripropionic acid; nitrilotris (methylenephosphonic acid) ; triethylenetetramine-N,N,N',N'',N''',N'''-hexaacetic acid; ethylenediamine-N,N'-bis(methylenephosphonic acid); ethylenediamine-di(o-hydroxyphenylacetic acid); 1,2-bis(2-aminophenoxy)ethane-N,N,N',N'-tetraacetic acid.

In accordance with the method of this invention, an excess amount of a Mg-chelating agent is added to the reactant solution whereby the measured value of the Mg ion content may be determined on the basis of the standard curve of a straight line. Accordingly, the Mg ion content in a sample to be examined may be determined accurately.

In the method of this invention, almost all the Mg ions as existing in a human body fluid sample to be examined are inactivated by the Mg-chelating agent as added to the reactant solution. Accordingly, this invention makes it possible to quickly and accurately perform a highly specific assay of Mg ions in the sample by utilizing the activity of isocitrate dehydrogenase which increases with the presence of even a small amount of the remaining Mg ions. The method of this invention can therefore assay magnesium accurately even in a very small amount of a sample to be examined.

The invention will now be described in further detail with reference to a couple of examples.

EXAMPLE 1

A standard solution containing 50 mg/dl of Mg ions was prepared by dissolving 41.9 mg of MgCl2.6H2O in 10 ml of purified water.

The standard solution was diluted in various ways to make solutions containing 0, 5, 10, 15, 20, 25, 30, 35, 40, 45 and 50 mg/dl, respectively, of Mg ions.

Then, 50 μl of each solution was added to 3 ml of a reactant solution of the composition shown below, and a variation of absorbance at 340 nm was determined by a rate assay at 37° C.

Composition of the reactant solution (37° C.):

| 100 mM | Tris-HCl having a pH of 8.0 |
| 20 mM | EDTA |
| 5 mM | Isocitrate |
| 5 mM | NADP$^+$ |
| 5 u/ml | iCDH (NADP$^+$) |

The results are shown in FIG. 2, which is a standard curve.

COMPARATIVE EXAMPLE

A standard solution containing 50 mg/dl of Mg ions was prepared by dissolving 41.9 mg of MgCl$_2$.6H$_2$O in 10 ml of purified water.

The standard solution was diluted in various ways to make solutions containing 0, 5, 10, 15, 20, 25, 30, 35, 40, 45 and 50 mg/dl, respectively, of Mg ions.

Then, 50 μl of each solution was added to 3 ml of a reactant solution of the composition shown below, and a variation of absorbance at 340 nm was determined by a rate assay at 37° C.

Composition of the reactant solution (37° C.):

| 100 mM | Tris-HCl having a pH of 8.0 |
| 5 mM | Isocitrate |
| 5 mM | NADP$^+$ |
| 0.04 u/ml | iCDH (NADP$^+$) |

The results are shown in FIG. 1, which, however, gives a tangent line and cannot be employed as a standard curve.

EXAMPLE 2

5 μl of a patient serum was added to 300 μl of a reactant solution of the composition shown below, and a variation of absorbance at 340 nm was determined by a rate assay at 37° C. to thereby obtain the magnesium concentration in the serum.

Next, using a commercial kit (Iatro Mg Rate; manufactured by Iatron Co.), the magnesium concentration in the patent serum was obtained. From the both values obtained, the relationship between the method of the invention and the method of using the commercial kit was investigated.

53 sera were examined in the manner mentioned above. A regression formula of y=1.05x −0.113 and a correlation coefficient of r=0.987 were obtained. The results were good.

Composition of the reactant solution (37° C.):

| 100 mM | Tris-HCl having a pH of 8.0 |
| 20 mM | EDTA |
| 5 mM | Isocitrate |
| 5 mM | NADP$^-$ |
| 5 u/ml | iCDH (NADP$^+$) |

EXAMPLE 3

A reactant solution (pH 8.0) comprising:

| EDTA | 20 mM |
| NADP$^-$ | 5 mM |
| Isocitric Acid | 5 mM |
| iCDH | 5 IU/ml |
| Tris-HCl | 100 mM | was charged into an automatic assay device (Cobas Fara II), where a human urine sample was assayed. A 5 mg/dl aqueous solution was used as the standard solution.

Precisely, 5 μl of the human urine sample to be examined was blended with 300 μl of the reactant solution and reacted at 37° C. The variation of the absorbance at 340 nm of the reaction system during the course of from one minute after initiation of the reaction to two minutes after the same was measured.

The human urine sample to be examined by the method was prepared as mentioned below.

10.3 mg/dl of a human fresh control urine for examination (EXA urine II, produced by Sankoh. Pure Chemical Co.) was blended with an aqueous magnesium solution having a known magnesium concentration in a proportion of 9/1, as mentioned below, to prepare five samples Nos. 1 to 5.

| | Aqueous Magnesium Solution | | | | |
|---|---|---|---|---|---|
| | 200 mg/dl 25 μl | 150 mg/dl 25 μl | 100 mg/dl 25 μl | 50 mg/dl 25 μl | 25 mg/dl 25 μl |
| Control Urine | 225 μl | 225 μl | 225 μl | 225 μl | 225 μl |
| Sample No. | 1 | 2 | 3 | 4 | 5 |

Methods of Calculation
Variation of Absorbance of Sample = ΔA

Variation of 5 mg/dl Standard Solution = $\Delta As$

Amount of Magnesium in Sample (mg/dl) = $(\Delta A/\Delta As) \times 5$

Results

| Sample No. | 1 | 2 | 3 | 4 | 5 |
|---|---|---|---|---|---|
| Theoretical Value in Sample (mg/dl) | 29.3 | 24.3 | 19.3 | 14.3 | 11.8 |
| Value Obtained by the Method of the Invention (mg/dl) | 29.6 | 23.2 | 19.3 | 14.2 | 12.4 |
| (Measured Value)/(Theoretical Value) (%) | 101 | 96 | 100 | 99 | 105 |

What is claimed is:

1. A method of assaying magnesium in a human body fluid, comprising adding a human body fluid sample to be examined to a reactant solution containing isocitrate dehydrogenase, NADP+, isocitrate and an excess amount of a chelating agent so that almost all Mg ions are bonded to the chelating agent whereupon the remaining Mg ions are reacted with NADP+ to form NADPH, and the amount of the thus formed NADPH is obtained by measuring the absorbance at 340 nm of the resulting solution immediately after addition of the human body fluid sample thereto, the amount of Mg ions in the human body fluid sample being thereby obtained from the thus measured absorbance value.

* * * * *